United States Patent
Schuessler

(10) Patent No.: US 10,080,879 B2
(45) Date of Patent: Sep. 25, 2018

(54) ENTERAL FEEDING CONNECTOR

(71) Applicant: KPR U.S., LLC, Mansfield, MA (US)

(72) Inventor: Wayne Schuessler, St. Louis, MO (US)

(73) Assignee: KPR U.S., LLC, Mansfield, MA (US)

( * ) Notice: Subject to any disclaimer, the term of this patent is extended or adjusted under 35 U.S.C. 154(b) by 0 days.

(21) Appl. No.: 14/863,654

(22) Filed: Sep. 24, 2015

(65) Prior Publication Data
US 2016/0089528 A1 Mar. 31, 2016

Related U.S. Application Data

(60) Provisional application No. 62/055,311, filed on Sep. 25, 2014.

(51) Int. Cl.
*A61M 39/10* (2006.01)

(52) U.S. Cl.
CPC ..... *A61M 39/10* (2013.01); *A61M 2039/1027* (2013.01); *A61M 2039/1033* (2013.01); *A61M 2039/1038* (2013.01); *A61M 2039/1066* (2013.01)

(58) Field of Classification Search
CPC ...... A61M 2039/1033; A61M 2039/10; A61M 2039/1038; A61M 2039/1027; A61M 2039/1066
See application file for complete search history.

(56) References Cited

U.S. PATENT DOCUMENTS 4,390,017 A 6/1983 Harrison et al.
4,878,516 A 11/1989 Mathieu
5,113,571 A 5/1992 Manska
6,699,233 B2 3/2004 Slanda et al.
(Continued)

FOREIGN PATENT DOCUMENTS

GB 2379253 A 3/2003

OTHER PUBLICATIONS

American National Standard Institute, "Small-bore connectors for liquids and gases in healthcare applications—Part 3: Connectors for enteral applications", Published by: Association for the Advancement of Medical Instrumentation 4301 N. Fairfax Drive, Suite 301 Arlington, VA 22203-1633 www.aami.org, © ISO/IEC 2013—All rights reserved, AAMI/ISO 80369-3, 43 pages.
(Continued)

*Primary Examiner* — Andrew Gilbert
*Assistant Examiner* — John Doubrava
(74) *Attorney, Agent, or Firm* — Adnan H. Bohri

(57) ABSTRACT

A medical tubing connector includes a first connector portion configured for connecting to a mating second connector. A tube engagement portion is integral with and opposite the first connector portion and configured for connecting to a medical tube. A liquid passage extends through the first connector portion and the tube engagement portion. The first connector portion includes a continuous outer surface for sealing engagement with the mating second connector. An annular portion is integral with and surrounds the male connector portion. A connecting portion connects the first connector portion to the annular portion. The connecting portion is discontinuous permitting liquid to pass through the connecting portion so that liquid is prevented from pooling between the first connector portion and the annular portion.

15 Claims, 15 Drawing Sheets

(56) References Cited

U.S. PATENT DOCUMENTS

| | | |
|---|---|---|
| 8,016,809 B2 | 9/2011 | Zinger et al. |
| 8,348,902 B2 | 1/2013 | Sugita et al. |
| 8,479,370 B2 | 7/2013 | Grant |
| 8,628,509 B2 | 1/2014 | Kropczynski, Jr. et al. |
| 9,814,871 B2 * | 11/2017 | Wlodarczyk ......... A61M 39/10 |
| 2006/0047251 A1 | 3/2006 | Bickford Smith et al. |
| 2006/0106349 A1 | 5/2006 | Kito et al. |
| 2007/0129705 A1 | 6/2007 | Trombley, III et al. |
| 2008/0045929 A1 | 2/2008 | Bimbach |
| 2012/0022457 A1 | 1/2012 | Silver |
| 2012/0150129 A1 | 6/2012 | Jin et al. |
| 2012/0157914 A1 | 6/2012 | Stroup |
| 2012/0245564 A1 | 9/2012 | Tekeste et al. |
| 2012/0330238 A1 | 12/2012 | Robert et al. |
| 2014/0246616 A1 | 9/2014 | Fangrow |
| 2015/0247597 A1 * | 9/2015 | Okiyama ............ A61M 39/045 285/317 |
| 2016/0067471 A1 * | 3/2016 | Ingram ................ A61M 39/20 604/533 |

OTHER PUBLICATIONS

International Search Report dated Nov. 30, 2015 in related International Application No. PCT/US2015/051909, 6 pages.
Written Opinion of the International Searching Authority dated Nov. 30, 2015 in related International Application No. PCT/US2015/051909, 6 pages.
"Alternate Syringes: Low Displacement Option," Rork Swisher, ISO 80369 Series Meeting, Berlin, Germany, Mar. 19, 2014, 11 pages.

* cited by examiner

ENTERAL FEEDING CONNECTOR

BACKGROUND

The present disclosure generally relates to an enteral feeding connector, and more particularly, to a small-bore enteral feeding connector including a fluid drain.

In a medical environment, many devices have tubing adapted for manual connection in order to provide a fluid connection between devices or between a device and a patient including enteral feeding pumps and enteral feeding lines. Each of these devices includes one or more connectors that a user or practitioner may connect together.

FIG. 1 shows a conventional enteral feeding connector assembly of the prior art including a male enteral feeding small-bore connector 1 and a female enteral feeding small-bore connector 3 configured to be connected to one another for use in connecting enteral fluid lines in healthcare applications. The enteral feeding connectors 1, 3 deliver fluid in the fluid lines through a fluid passage 5 extending through the connectors. Fluid is typically delivered from the female connector 3 to the male connector 1. The male enteral feeding small-bore connector 1 includes a well 7 located at an end of the male connector that engages with the female connector 3 for threadably connecting the male connector with the female connector. A problem with enteral feeding connectors of this type is that when the female connector 3 is separated from the male connector 1, after fluid has been delivered through the connectors, fluid can collect in the well 7 of the male connector. This exposed fluid can become contaminated by the surrounding environment. When the connectors 1, 3 are subsequently reconnected (FIG. 2), the contaminated fluid can be forced into the fluid passage 5 of the connectors and delivered to the patient.

SUMMARY

In one aspect, a medical tubing connector generally comprises a first connector portion configured for connecting to a mating second connector. A tube engagement portion is integral with and opposite the first connector portion and configured for connecting to a medical tube. A liquid passage extends through the first connector portion and the tube engagement portion. The first connector portion includes a continuous outer surface for sealing engagement with the mating second connector. An annular portion is integral with and surrounds the first connector portion. A connecting portion connects the first connector portion to the annular portion. The connecting portion is discontinuous permitting liquid to pass through the connecting portion so that liquid is prevented from pooling between the first connector portion and the annular portion.

In some embodiments, the discontinuity comprises an open area of the connecting portion.

In certain embodiments, the open area of the connecting portion extends over at least 40% of the connecting portion.

In some embodiments, the open area of the connecting portion extends over at least 80% of the connecting portion.

In certain embodiments, the connecting portion is defined by spaced apart connecting arms extending between the first connector portion and the annular portion.

In some embodiments, the connecting portion comprises a floor extending circumferentially around the first connector portion, the floor defining a plurality of openings permitting liquid to pass through the connecting portion.

In certain embodiments, the openings are circumferentially spaced around the connecting portion.

In some embodiments, the openings comprise circular holes in the floor.

In certain embodiments, the openings comprise oblong slots in the floor.

In some embodiments, the slots extend at least partially along the annular portion.

In certain embodiments, the annular portion comprises a threaded inner surface for mating with threads on the mating second connector.

In some embodiments, the connector comprises a small-bore connector.

In certain embodiments, the first connector portion, the tube engagement portion, and the annular portion are formed as one piece of material.

In some embodiments, the first connector portion is continuous such that the first connector portion is free of any channels or grooves in the outer surface of the first connector portion.

In another aspect, a male enteral feeding connector generally comprises a first connector portion configured for connecting to a female enteral feeding connector. A tube engagement portion is integral with and opposite the first connector portion and configured for connecting to an enteral feeding tube for delivering enteral feeding fluid to a patient. A liquid passage extends through the first connector portion and the tube engagement portion. The first connector portion includes a continuous outer surface for sealing engagement with the female enteral feeding connector. An annular portion is integral with and surrounds the first connector portion. A connecting portion connects the first connector portion to the annular portion. The connecting portion is discontinuous permitting liquid to pass through the connecting portion so that liquid is prevented from pooling between the first connector portion and the annular portion.

In certain embodiments, the discontinuity of the connecting portion comprises an open area of the connecting portion.

In some embodiments, the connecting portion is defined by spaced apart connecting arms extending between the first connector portion and the annular portion.

In certain embodiments, the connecting portion comprises a floor extending circumferentially around the first connector portion, the floor defining a plurality of openings permitting liquid to pass through the connecting portion.

In some embodiments, the openings are circumferentially spaced around the connecting portion.

In certain embodiments, the connector comprises a small-bore connector.

In some embodiments, the first connector portion, the tube engagement portion, and the annular portion are formed as one piece of material.

In certain embodiments, the male enteral feeding connector is in combination with the female enteral feeding connector.

In some embodiments, the first connector portion is continuous such that the first connector portion is free of any channels or grooves in the outer surface of the first connector portion.

In another aspect, an enteral feeding connector generally comprises a first connector portion configured for connecting to a mating second connector. A tube engagement portion is integral with and opposite the first connector portion and configured for connecting to a medical tube. A liquid passage extends through the first connector portion and the tube engagement portion. The first connector portion includes a continuous outer surface for sealing engagement with the mating second connector. An annular portion is integral with and surrounds the first connector portion. A connecting portion connects the first connector portion to the annular portion. A drain between the first connector portion and the annular portion prevents fluid from pooling between the first connector portion and the annular portion.

Other objects and features will be in part apparent and in part pointed out hereinafter.

DESCRIPTION OF THE DRAWINGS

Corresponding reference characters indicate corresponding parts throughout the drawings.

DETAILED DESCRIPTION

Figure 1:
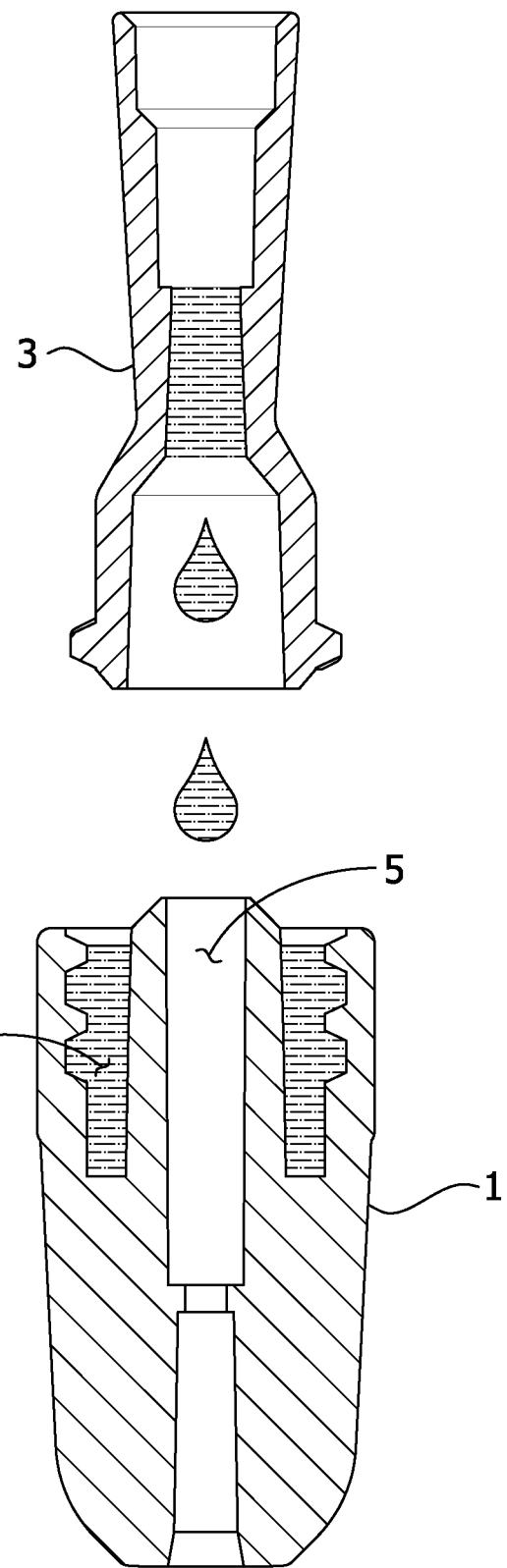
FIG. 1 is a cross section of a prior art enteral feeding connection assembly in a disconnected configuration illustrating fluid collection in a well in the assembly.
Figure 2:
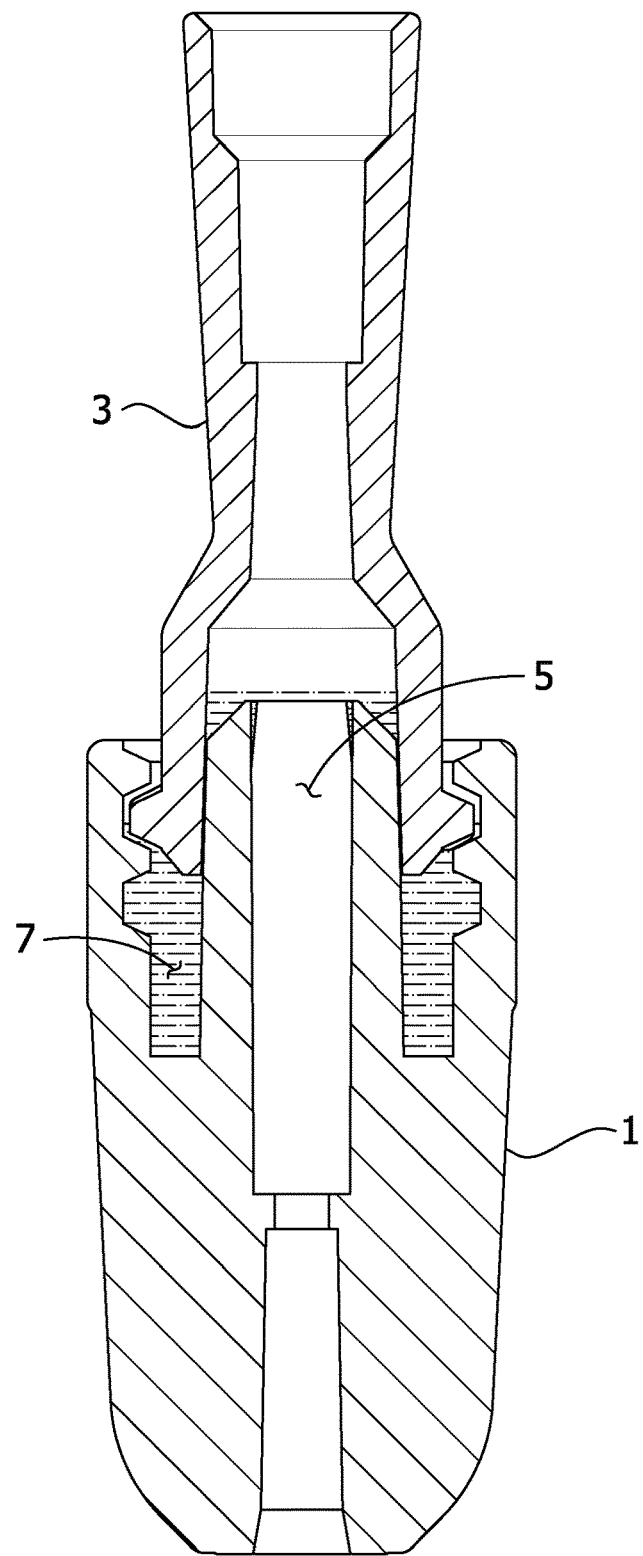
FIG. 2 is a cross section of the prior art enteral feeding connection assembly of FIG. 1 in a connected configuration.
Figure 3:
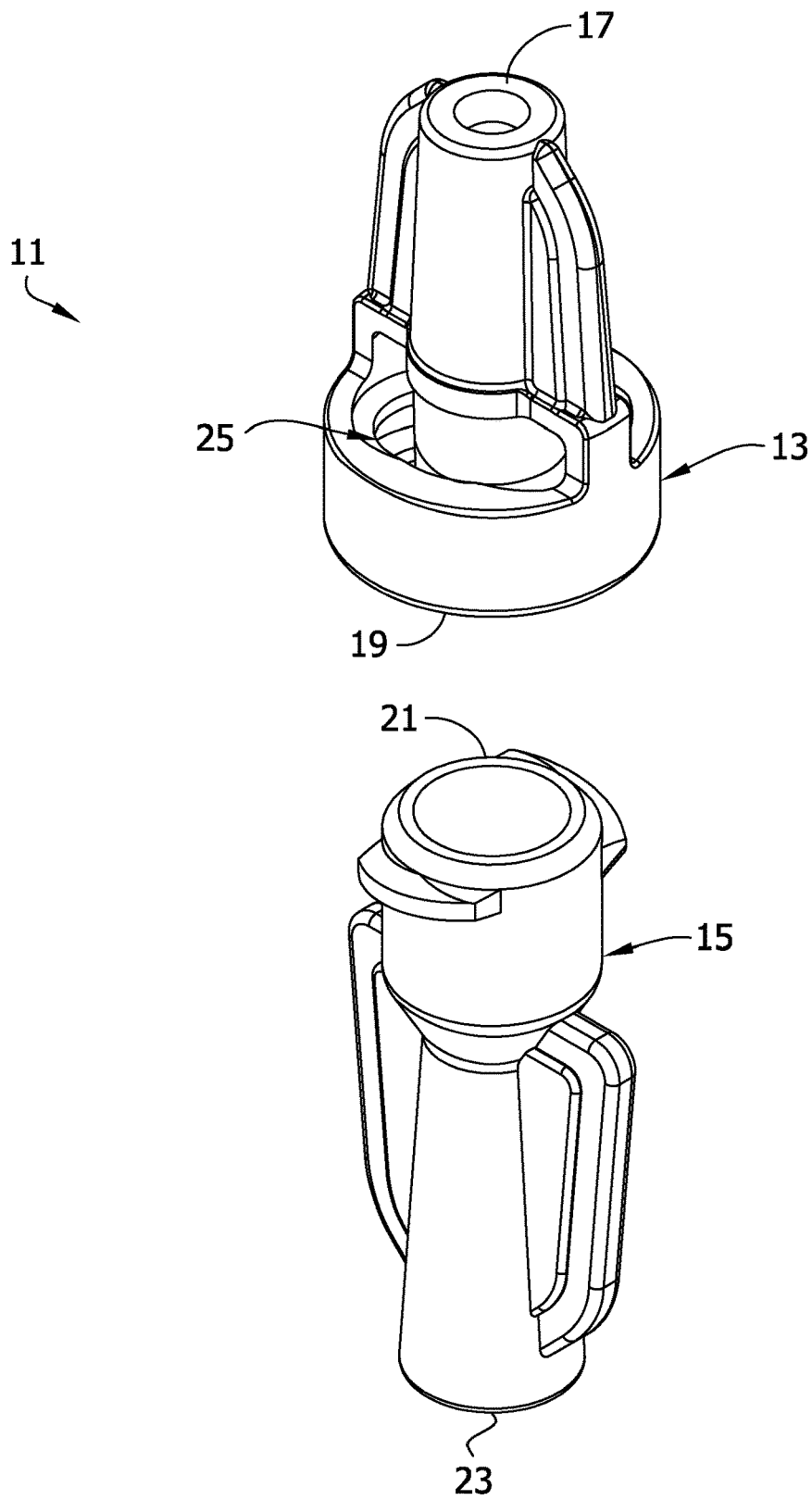
FIG. 3 is a perspective of an enteral feeding connector assembly.

Referring now to FIG. 3, an enteral feeding connector assembly is generally indicated at 11. The assembly comprises a male enteral feeding small-bore connector 13 and a female enteral feeding small-bore connector 15 configured to connect to the male enteral feeding small-bore connector. The male enteral feeding small-bore connector 13 may be configured to connect to tubing (not shown) that interfaces with a patient at a tube connection end 17 of the male enteral feeding small-bore connector, and connect to the female enteral feeding small-bore connector 15 at a connector end 19 of the male enteral feeding small-bore connector. The female enteral feeding small-bore connector 15 may be configured to connect to the male enteral feeding small-bore connector 13 at a connector end 21 of the female enteral feeding small-bore connector, and connect to tubing (not shown) from a fluid source (e.g., nutrient bag) at a tube connection end 23 of the female enteral feeding small-bore connector. The male enteral feeding small-bore connector 13 may include a drain 25 permitting fluid to drain out of the connector as will be explained in greater detail below.

The connector ends 19, 21 of the enteral feeding connectors 13, 15 may be discriminating connectors such that they are incompatible with any other small-bore connectors. It is also envisioned that other types of enteral feeding connectors can be used. For instance, luer-type enteral feeding connectors are also within the scope of the disclosure.

Figure 4:
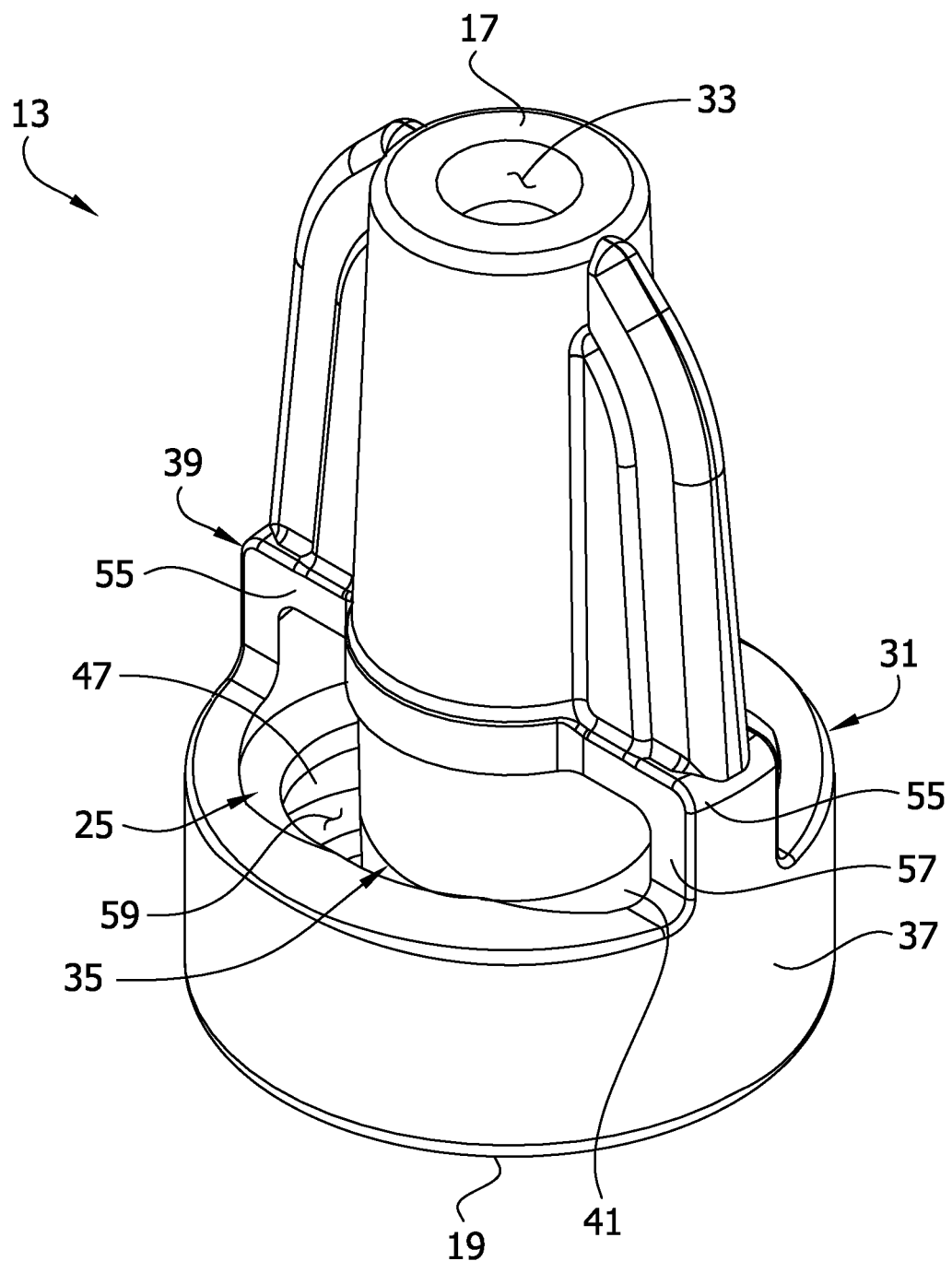
FIG. 4 is a perspective of a male enteral feeding connector of the assembly of FIG. 3.
Figure 5:
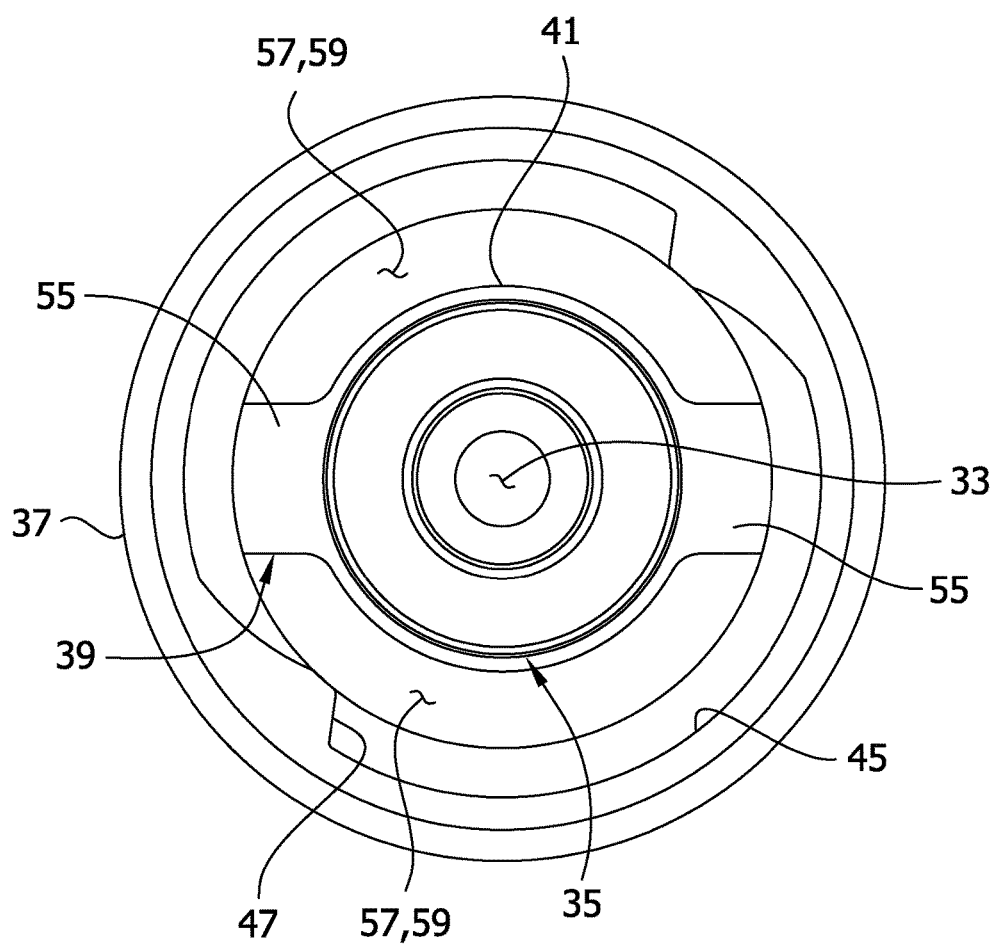
FIG. 5 is a front end view of the male enteral feeding connector of FIG. 4.
Figure 6:
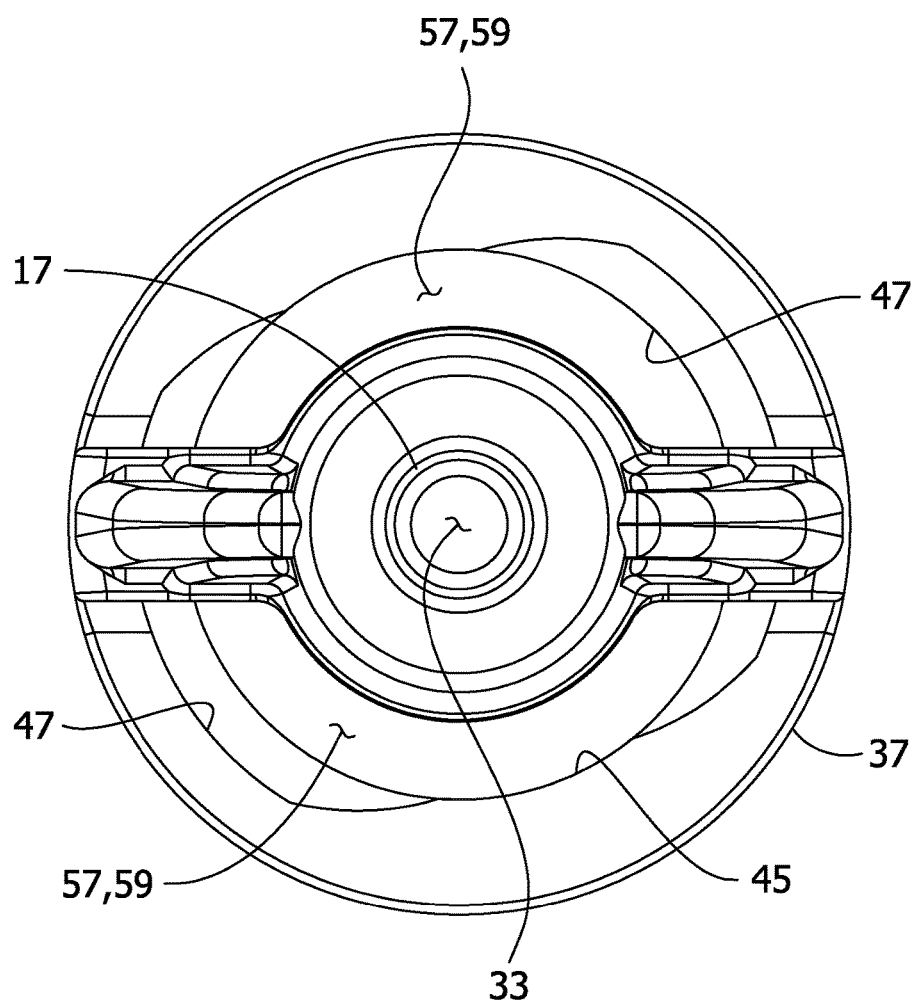
FIG. 6 is a rear end view of the male enteral feeding connector of FIG. 4.
Figure 7:
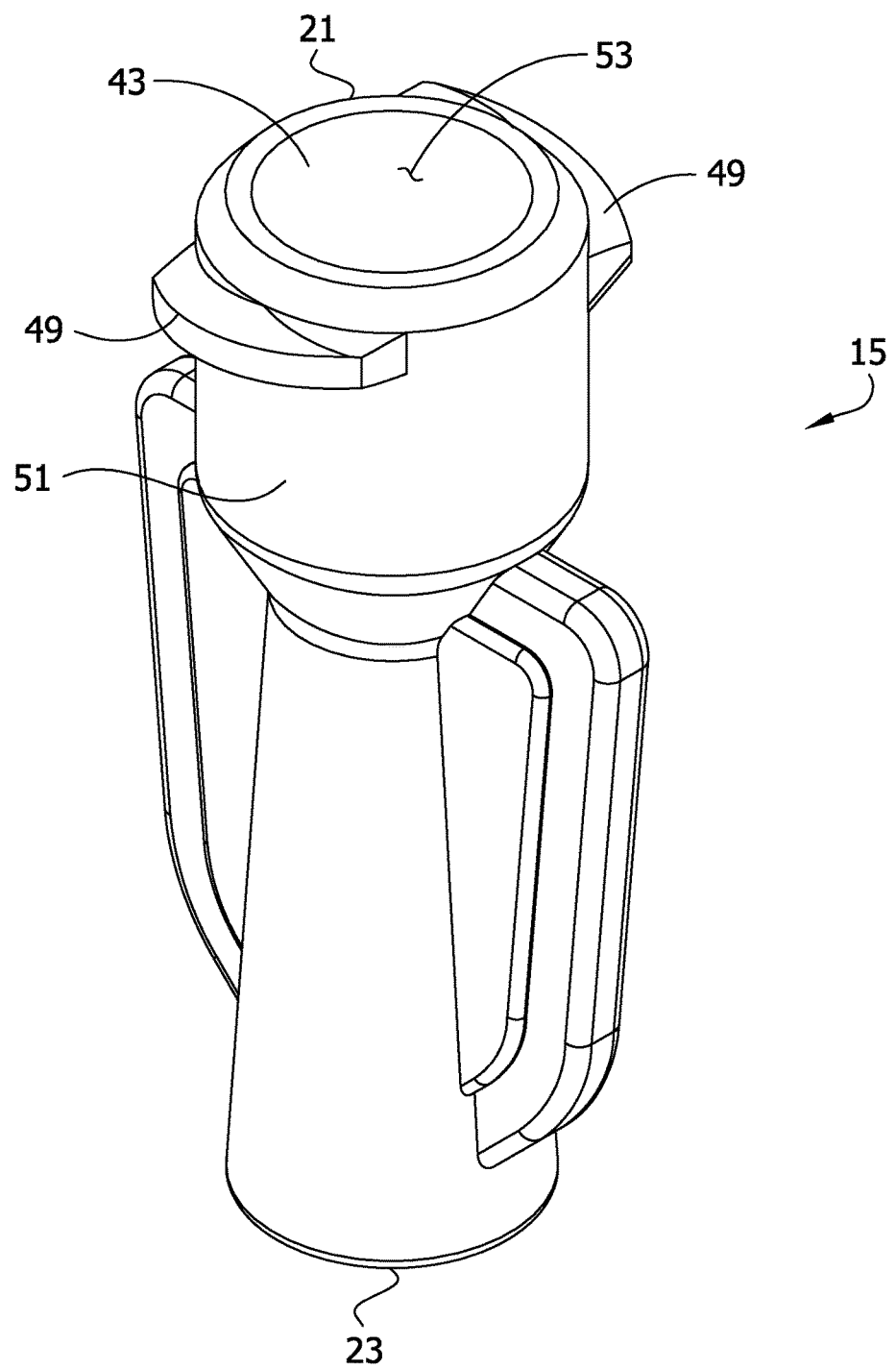
FIG. 7 is an enlarged perspective of a female enteral feeding connector of the assembly of FIG. 3.
Figure 8A:
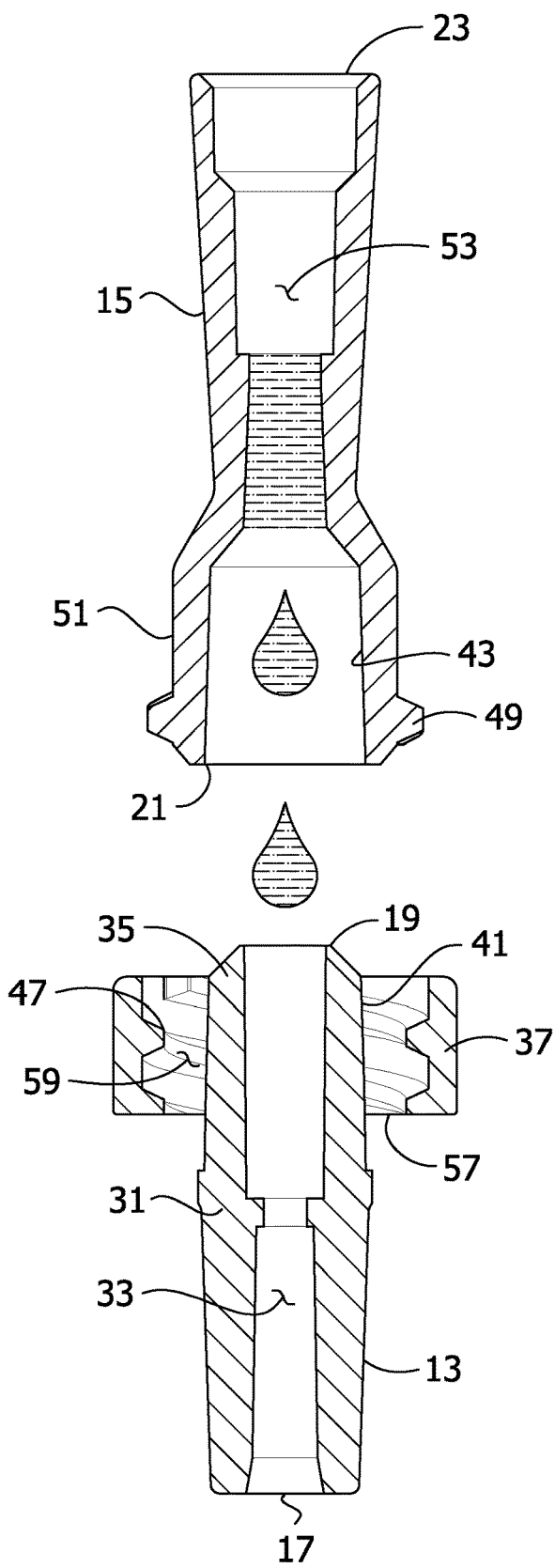
FIG. 8A is a section of the male enteral feeding connector disconnected from the female enteral feeding connector.
Figure 8B:
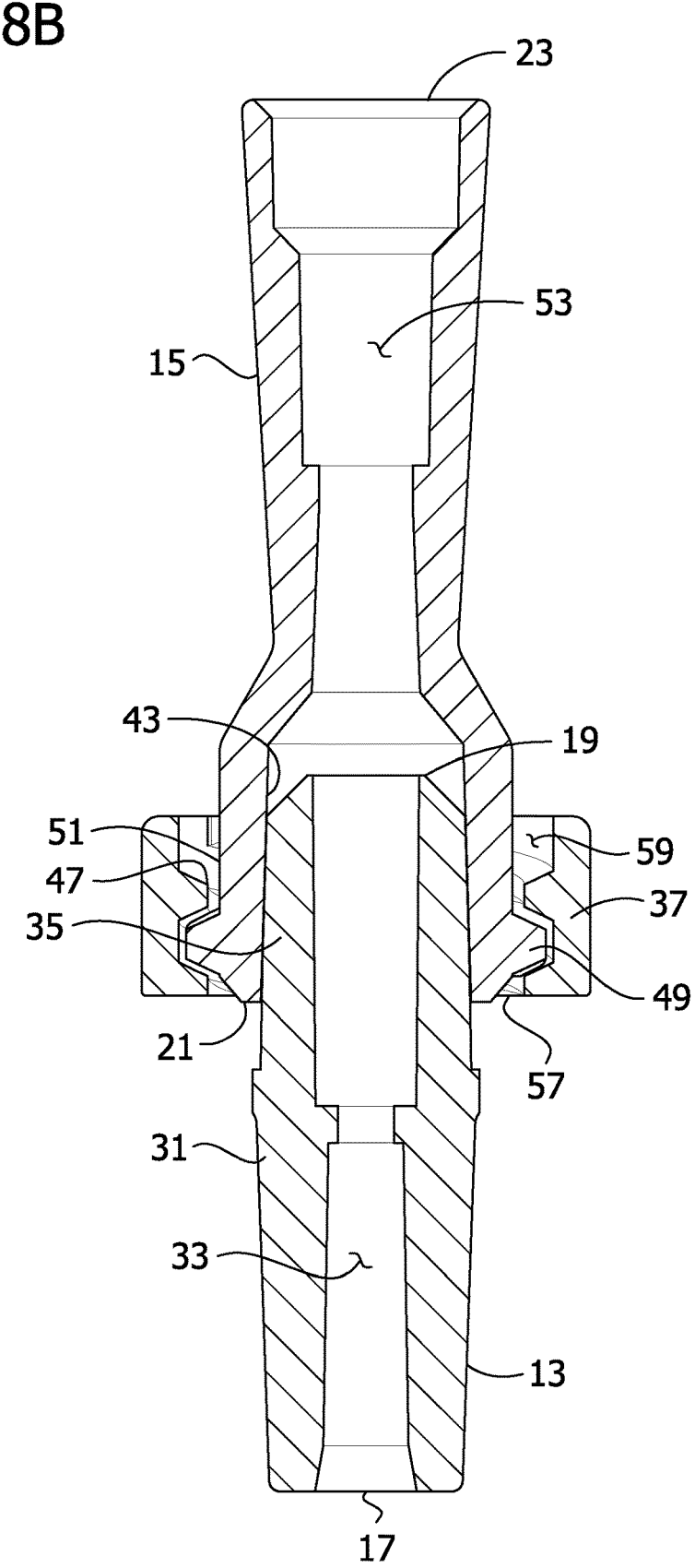
FIG. 8B is a section of the male enteral feeding connector connected to the female enteral feeding connector.

Referring to FIGS. 4-6, the male enteral feeding small-bore connector 13 may comprise a connector body 31 including the connector end 19, the tube connection end 17, and a fluid passage 33 extending through the connector body from the connector end to the tube connection end. The connector end 19 of the connector body 31 may comprise a male connector portion 35 defining a part of the fluid passage 33, an annular portion 37 surrounding the male connector portion, and a connecting portion 39 connecting the annular portion to the male connector portion. An outer surface 41 of the male connector portion 35 may be configured for sealing engagement with an inner surface 43 of the connector end 21 of the female enteral feeding small-bore connector 15 (FIGS. 7 and 8B). For instance, the outer surface 41 of the male connector portion 35 may have a continuous profile such that the male connector portion is free of any channels or grooves in the outer surface of the male connector portion. An inner surface 45 of the annular portion 37 may include threads 47 for engaging threads 49 on an outer surface 51 of the connector end 21 of the female connector 15 for securely engaging the male enteral feeding small-bore connector 13 with the female enteral feeding small-bore connector. Connection of the male and female enteral feeding small-bore connectors 13, 15 establishes fluid communication between the fluid passage 33 in the male connector and a fluid passage 53 in the female connector.

The connecting portion 39 may comprise a pair of spaced apart connecting arms 55 extending between the male connector portion 35 and the annular portion 37. A pair of arcuate openings 57 at sides of the connecting arms 55 may communicate with an interior space 59 of the annular portion 37 to create secondary passages around the male connector portion 35 and past the connecting portion 39. In the illustrated embodiment, the openings 57 allow fluid to pass from the interior space 59 of the annular portion 37 directly through the connecting portion 39 without being obstructed by structure of the male connector 13. Therefore, when the female connector 15 is separated from the male connector 13, after fluid has been delivered through the connectors, a substantial amount of fluid cannot collect within the interior space 59 of the annular portion 37 (FIG. 8A). Instead, the openings 57 allow the fluid to pass through the connecting portion 39 preventing the fluid from pooling and potentially becoming contaminated. Thus, when the connectors 13, 15 are reconnected (FIG. 8B), there is no or very little fluid within the interior space 59 of the annular portion 37 so that no fluid is forced from the annular portion interior space into the fluid passages 33, 53 and delivered to the patient.

The spaced apart connecting arms 55 form a discontinuity in the connecting portion 39 which provides an open area for fluid to pass through the connecting portion. In the illustrated embodiment, the discontinuity extends over about 80% of the connecting portion 39. The discontinuity can be defined by the open space extending from the sides of the connecting arms 55 circumferentially around the male connector portion 35. The discontinuity of the connecting portion 39 could be greater or lesser than 80% depending on an extent to which the connecting arms 55 extend in the circumferential direction and/or the number of connecting arms. For example, in one or more embodiments, the discontinuity can be greater than 40%.

Figure 9:
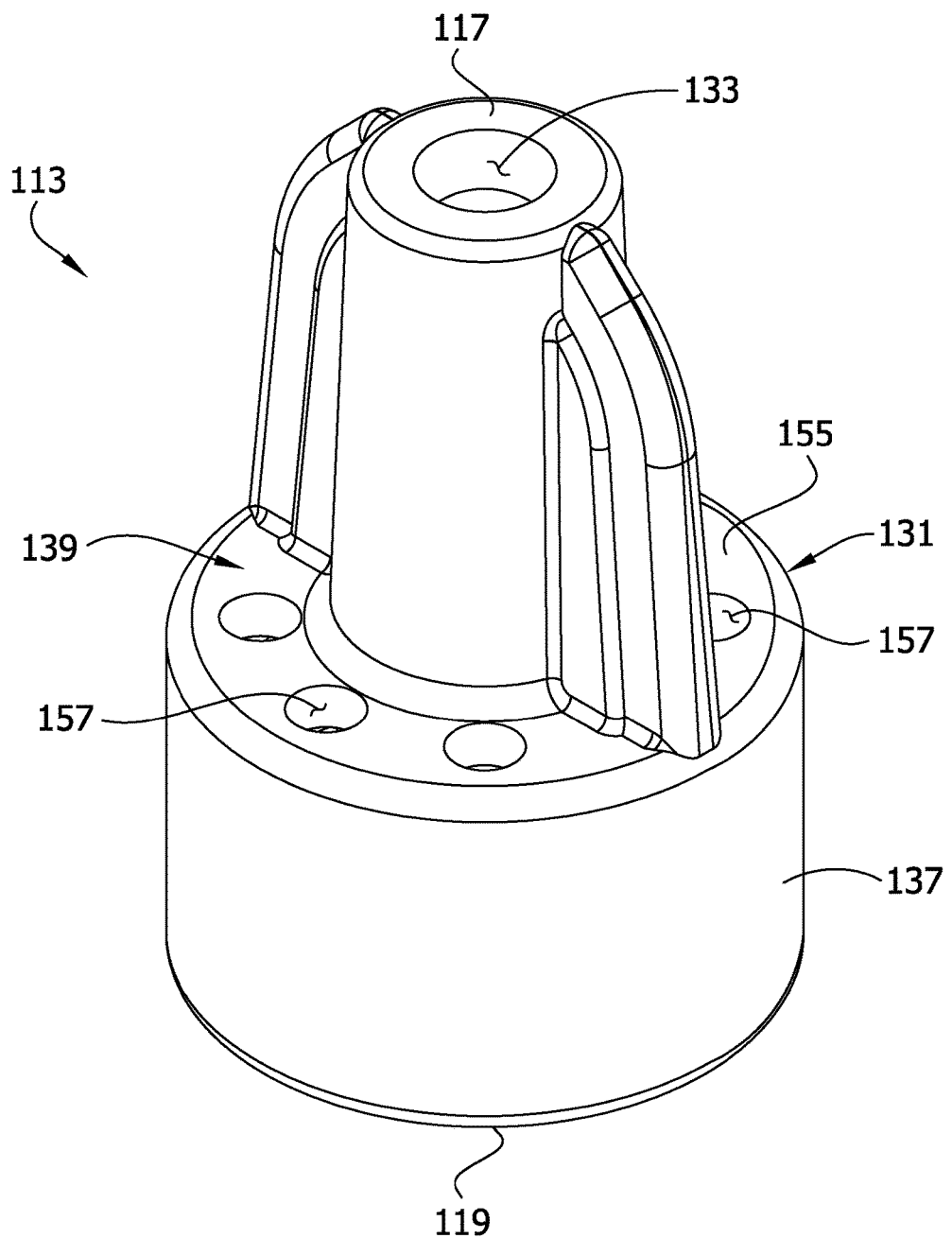
FIG. 9 is a perspective of another male enteral feeding connector.
Figure 10:
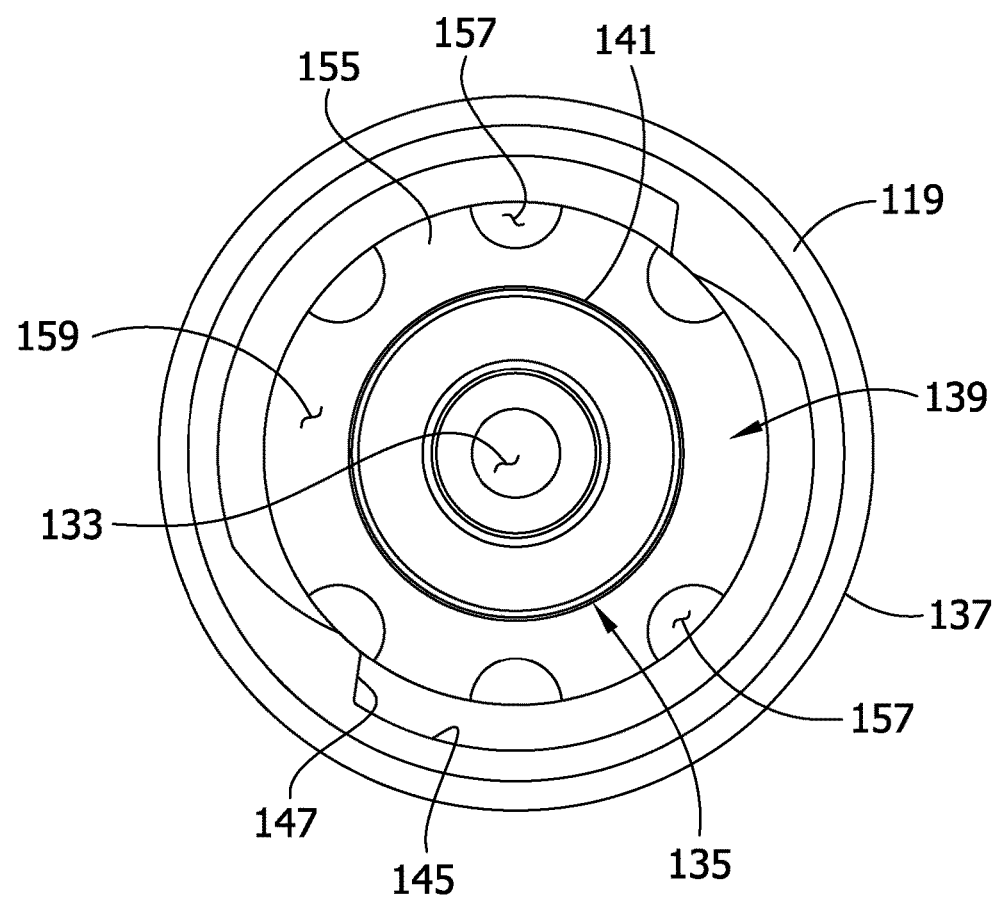
FIG. 10 is a front end view of the male enteral feeding connector of FIG. 9.
Figure 11:
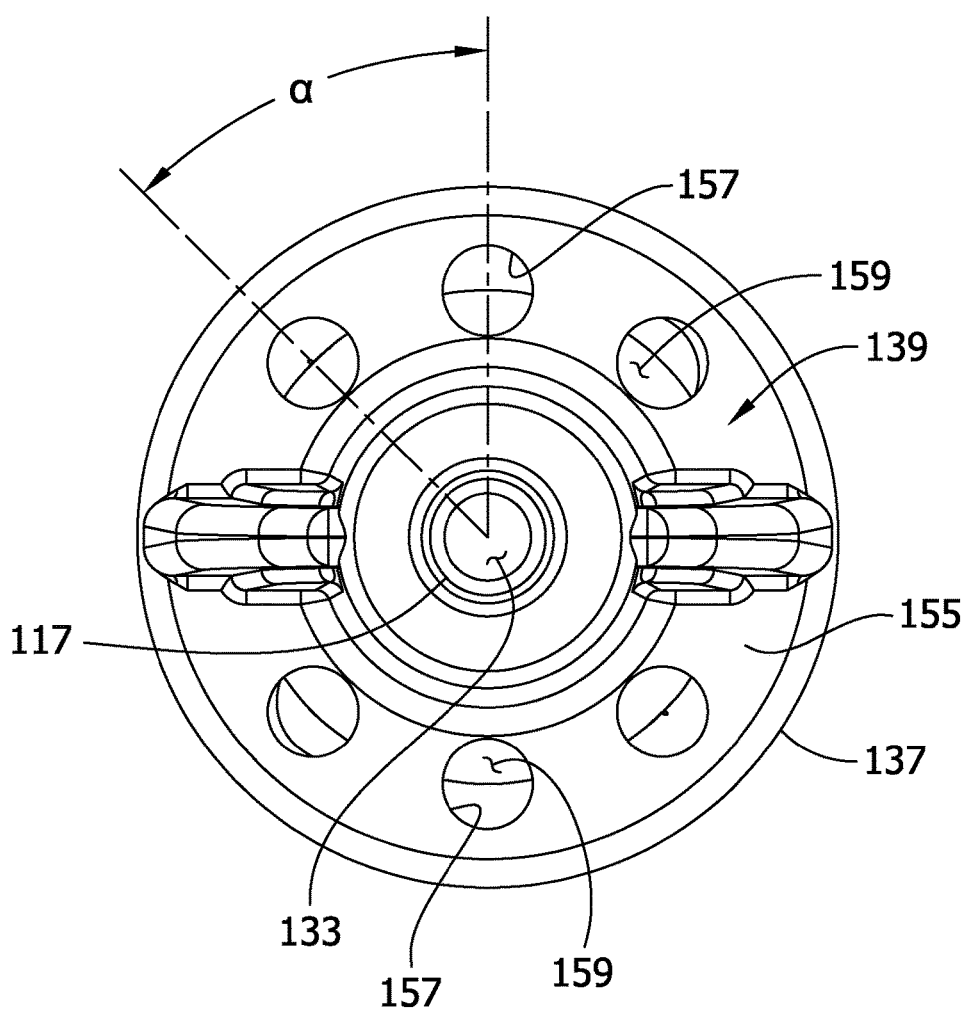
FIG. 11 is a rear end view of the male enteral feeding connector of FIG. 9.

Referring to FIGS. 9-11, a male enteral feeding small-bore connector 113 may comprise a connector body 131 including a connector end 119, a tube connection end 117, and a fluid passage 133 extending through the connector body from the connector end to the tube connection end. The connector end 119 of the connector body 131 may comprise a male connector portion 135 (FIG. 10) defining a part of the fluid passage 133, an annular portion 137 surrounding the male connector portion, and a connecting portion 139 connecting the annular portion to the male connector portion. An outer surface 141 of the male connector portion 135 may be configured for sealing engagement with the inner surface 43 of the connector end 21 of the female enteral feeding small-bore connector 15 (FIG. 7). For instance, the outer surface 141 of the male connector portion 135 may have a continuous profile such that the male connector portion is free of any channels or grooves in the outer surface of the male connector portion. An inner surface 145 of the annular portion 137 may include threads 147 for engaging the threads 49 on the outer surface 51 of the connector end of the female connector 15 for securely engaging the male enteral feeding small-bore connector 113 with the female enteral feeding small-bore connector. Connection of the male and female enteral feeding small-bore connectors 113, 15 establishes fluid communication between the fluid passage 133 in the male connector and the fluid passage 53 in the female connector.

The connecting portion 139 may comprise an annular floor 155 extending circumferentially around the male connector portion 135 between the male connector portion and the annular portion 137. A plurality of openings 157 extending through the floor 155 may communicate with an interior space 159 of the annular portion 137 to create secondary passages around the male connector portion 135 and past the connecting portion 139. The openings 157 may comprise circular holes that are circumferentially spaced around the connecting portion 139. Other opening shapes are also envisioned. Adjacent openings 157 may be spaced by an angle α about 45 degrees from each other (FIG. 11). Other degrees of spacing are also envisioned.

In the illustrated embodiment, the openings 157 allow fluid to pass from the interior space 159 of the annular portion 137 through the connecting portion 139. Therefore, when the female connector 15 is separated from the male connector 113, after fluid has been delivered through the connectors, a substantial amount of fluid cannot collect within the interior space 159 of the annular portion 137. Instead, the openings 157 allow the fluid to pass through the connecting portion 139 preventing the fluid from pooling and potentially becoming contaminated. Thus, when the connectors 113, 15 are reconnected, there is no or very little fluid within the interior space 159 of the annular portion 137 so that no fluid is forced from the annular portion interior space into the fluid passages 133, 53 and delivered to the patient.

The openings 157 in the floor 155 form a discontinuity in the connecting portion 139 which provides an open area for fluid to pass through the connecting portion. In the illustrated embodiment, the discontinuity extends over about 35% of the connecting portion 139. The discontinuity can be defined by the open spaces formed by the openings 157. The discontinuity of the connecting portion 139 could be greater or lesser than 35% depending on the size and/or the number of the openings 157.

Figure 12:
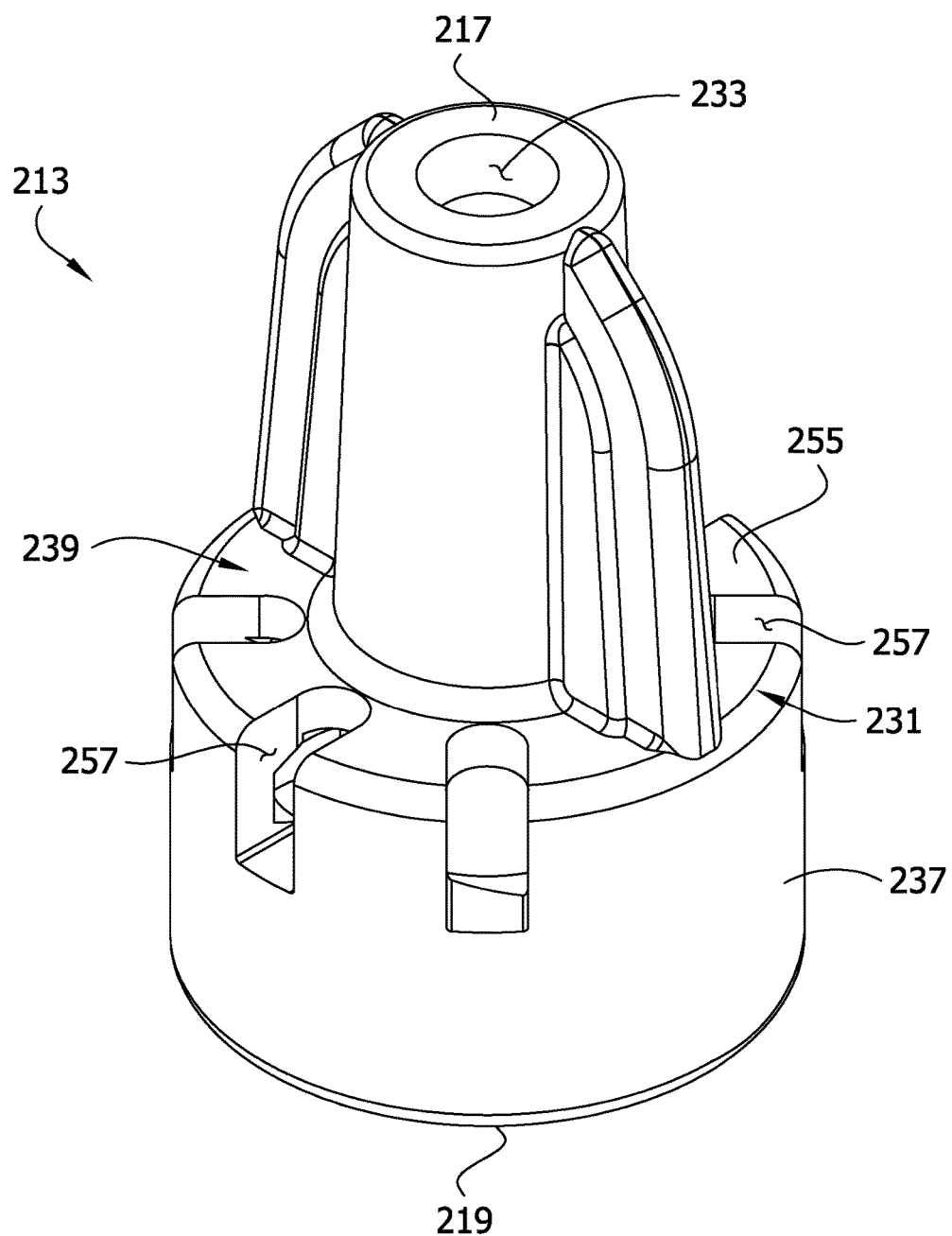
FIG. 12 is a perspective of another male enteral feeding connector.
Figure 13:
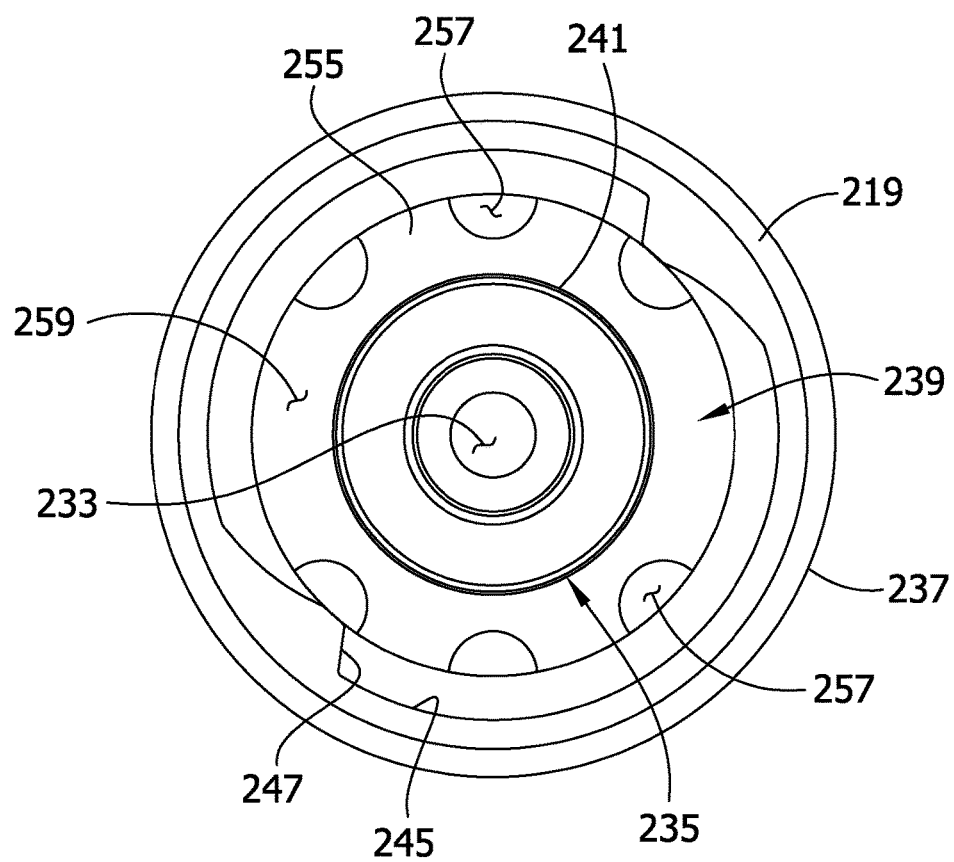
FIG. 13 is a front end view of the male enteral feeding connector of FIG. 12.
Figure 14:
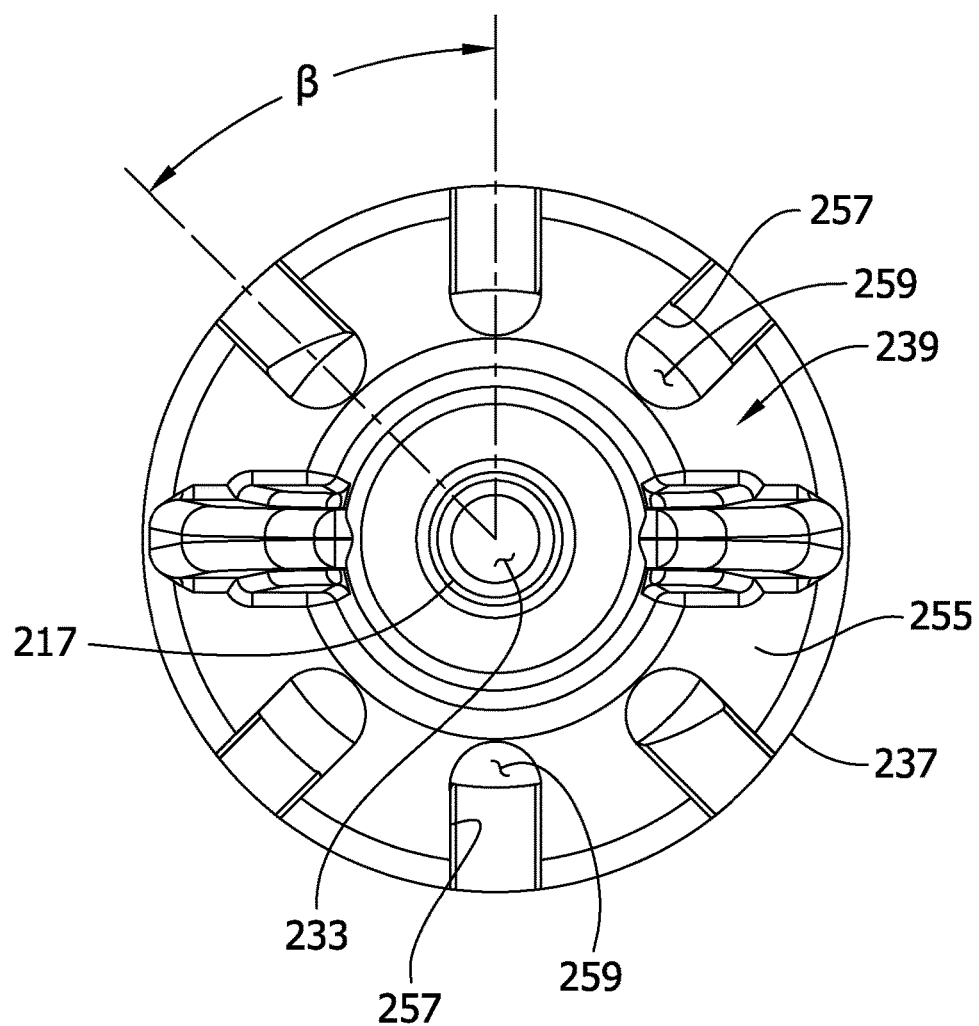
FIG. 14 is a rear end view of the male enteral feeding connector of FIG. 12.

Referring to FIGS. 12-14, a male enteral feeding small-bore connector 213 may comprise a connector body 231 including a connector end 219, a tube connection end 217, and a fluid passage 233 extending through the connector body from the connector end to the tube connection end. The connector end 219 of the connector body 231 may comprise a male connector portion 235 defining a part of the fluid passage 233, an annular portion 237 surrounding the male connector portion, and a connecting portion 239 connecting the annular portion to the male connector portion. An outer surface 241 of the male connector portion 235 may be configured for sealing engagement with the inner surface 43 of the connector end 21 of the female enteral feeding small-bore connector 15 (FIG. 7). For instance, the outer surface 241 of the male connector portion 235 may have a continuous profile such that the male connector portion is free of any channels or grooves in the outer surface of the male connector portion. An inner surface 245 of the annular portion 237 may include threads 247 for engaging the threads 49 on the outer surface 51 of the connector end of the female connector 15 for securely engaging the male enteral feeding small-bore connector with the female enteral feeding small-bore connector. Connection of the male and female enteral feeding small-bore connectors 213, 15 establishes fluid communication between the fluid passage 233 in the male connector and the fluid passage 53 in the female connector.

The connecting portion 239 may comprise an annular floor 255 extending circumferentially around the male connector portion 235 between the male connector portion and the annular portion 237. A plurality of slots 257 extending through the floor 255 may communicate with an interior space 259 of the annular portion 237 to create secondary passages around the male connector portion 235 and past the connecting portion 239. The slots 257 may comprise oblong holes that are circumferentially spaced around the connecting portion 239 and extend radially along the connecting portion. A portion of each slot 257 may also extend continuously from the connector portion 239 longitudinally along the annular portion 237 increasing a total open area of the slots. Other slot configurations are also envisioned. Adjacent slots 257 may be spaced by angle β about 45 degrees from each other (FIG. 14). Other degrees of spacing are also envisioned.

In the illustrated embodiment, the slots 257 allow fluid to pass from the interior space 259 of the annular portion 237 through the connecting portion 239 and annular portion 237. Therefore, when the female connector 15 is separated from the male connector 213, after fluid has been delivered through the connectors, a substantial amount of fluid cannot collect within the interior space 259 of the annular portion 237. Instead, the slots 257 allow the fluid to pass through the connecting portion 239 and annular portion 237 preventing the fluid from pooling and potentially becoming contaminated. Thus, when the connectors 213, 15 are reconnected, there is no or very little fluid within the interior space 259 of the annular portion 237 so that no fluid is forced from the annular portion interior space into the fluid passages 233, 53 and delivered to the patient.

The slots 257 in the floor 255 form a discontinuity in the connecting portion 239 which provides an open area for fluid to pass through the connecting portion. In the illustrated embodiment, the discontinuity extends over about 35% of the connecting portion 239. The discontinuity can be defined by the open spaces formed by the slots 257. The discontinuity of the connecting portion 239 could be greater or lesser than 35% depending on the size and/or the number of the slots 257.

When introducing elements or the preferred embodiments, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several technical effects are achieved and other advantageous results attained.

As various changes could be made in the above constructions and methods, it is intended that all matter contained in the above description and shown in the accompanying drawings shall be interpreted as illustrative and not in a limiting sense.

What is claimed is:

1. A medical tubing connector comprising:
    a first connector portion configured for connecting to a mating second connector;
    a tube engagement portion integral with and opposite the first connector portion and configured for connecting to a medical tube;
    a liquid passage extending along an axis through the first connector portion and the tube engagement portion, the first connector portion including a continuous outer surface for sealing engagement with the mating second connector;
    an annular portion integral with and surrounding the first connector portion, and
    a connecting portion connecting the first connector portion to the annular portion, the connecting portion including a discontinuity permitting liquid to pass through the connecting portion so that liquid is prevented from pooling between the first connector portion and the annular portion;
    wherein the connecting portion is defined by spaced apart connecting arms extending between the first connector portion and the annular portion, each connecting arm comprising a first section extending from an end wall of the annular portion and a second section projecting from the first section and extending from the first section in a direction transverse to the first section to the first connector portion, the second section engaging the first connector portion at a location axially spaced from the annular portion by the first section, the first section having exposed side surfaces and an exposed inwardly facing surface, the exposed inwardly facing surface being separated from the first connector portion by an open space, and the second section having exposed side surfaces and an exposed axially facing surface, the exposed axially facing surface being separated from the annular portion by the open space.

2. The connector of claim 1, wherein the discontinuity comprises an open area of the connecting portion.

3. The connector of claim 2, wherein the open area of the connecting portion extends over at least 40% of the connecting portion.

4. The connector of claim 3, wherein the open area of the connecting portion extends over at least 80% of the connecting portion.

5. The connector of claim 1, wherein the annular portion comprises a threaded inner surface for mating with threads on the mating second connector.

6. The connector of claim 1, wherein the connector comprises a small-bore connector.

7. The connector of claim 1, wherein the first connector portion, the tube engagement portion, and the annular portion are formed as one piece of material.

8. The connector of claim 1, wherein the first connector portion is continuous such that the first connector portion is free of any channels or grooves in the outer surface of the first connector portion.

9. The connector of claim 1, wherein the connecting arms directly oppose each other along a circumference of the annular portion.

10. The connector of claim 1, wherein the connecting arms directly oppose each other along an upper circumference of the annular portion.

11. A male enteral feeding connector, comprising:
    a first connector portion configured for connecting to a female enteral feeding connector;
    a tube engagement portion integral with and opposite the first connector portion and configured for connecting to an enteral feeding tube for delivering enteral feeding fluid to a patient;
    a liquid passage extending along an axis through the first connector portion and the tube engagement portion, the first connector portion including a continuous outer surface for sealing engagement with the female enteral feeding connector;
    an annular portion integral with and surrounding the first connector portion; and
    a connecting portion connecting the first connector portion to the annular portion, the connecting portion being discontinuous permitting liquid to pass through the connecting portion so that liquid is prevented from pooling between the first connector portion and the annular portion,
    wherein the connecting portion is defined by spaced apart connecting arms extending between the first connector portion and the annular portion, each connecting arm comprising a first section extending from an end wall of the annular portion and a second section projecting from the first section and extending from the first section in a direction transverse to the first section to the first connector portion, the second section engaging the first connector portion at a location axially spaced from the annular portion by the first section, the first section having exposed side surfaces and an exposed inwardly facing surface, the exposed inwardly facing surface being separated from the first connector portion by an open space, and the second section having exposed side surfaces and an exposed axially facing surface, the exposed axially facing surface being separated from the annular portion by the open space.

12. The connector of claim 11, wherein the discontinuity of the connecting portion comprises an open area of the connecting portion.

13. The connector of claim 11, further comprising the female enteral feeding connector.

14. The connector of claim 11, wherein the connecting arms directly oppose each other along a circumference of the annular portion.

15. The connector of claim 11, wherein the connecting arms directly oppose each other along an upper circumference of the annular portion.

* * * * *